United States Patent
Zhang et al.

(12)

(10) Patent No.: US 6,608,715 B2
(45) Date of Patent: Aug. 19, 2003

(54) WAVELENGTH CONVERTER USING BRAGG-GRATING

(75) Inventors: Jianjun Zhang, Cupertino, CA (US);
Peiching Ling, San Jose, CA (US);
Jinliang Chen, Saratoga, CA (US);
Ming Xu, San Jose, CA (US)

(73) Assignee: Integrated Optics Communications Corporation, Sunnyvale, CA (US)

( * ) Notice: Subject to any disclaimer, the term of this patent is extended or adjusted under 35 U.S.C. 154(b) by 0 days.

(21) Appl. No.: 10/256,480

(22) Filed: Sep. 26, 2002

(65) Prior Publication Data

US 2003/0107798 A1 Jun. 12, 2003

Related U.S. Application Data

(63) Continuation-in-part of application No. 10/202,054, filed on Jul. 23, 2002, and a continuation-in-part of application No. 10/190,018, filed on Jul. 5, 2002, and a continuation-in-part of application No. 10/188,955, filed on Jul. 3, 2002, and a continuation-in-part of application No. 10/177,632, filed on Jun. 19, 2002, and a continuation-in-part of application No. 10/104,273, filed on Mar. 22, 2002.

(60) Provisional application No. 60/373,803, filed on Apr. 19, 2002, and provisional application No. 60/348,927, filed on Oct. 22, 2001.

(51) Int. Cl.[7] ............................... G02F 2/02; G02B 6/293
(52) U.S. Cl. ........................ 359/332; 359/326; 385/24
(58) Field of Search ................................ 359/326–332; 385/24, 37

(56) References Cited

U.S. PATENT DOCUMENTS

2002/0024717 A1 * 2/2002 Nakamura ................. 359/326
2002/0063944 A1 * 5/2002 Kim et al. ................. 359/326

FOREIGN PATENT DOCUMENTS

| JP | 2-151842 | * 6/1990 | ............ G02F/2/02 |
| JP | 2001-324734 | * 11/2001 | ............ G02F/1/365 |

* cited by examiner

*Primary Examiner*—John D. Lee
(74) *Attorney, Agent, or Firm*—Perkins Coie, LLP

(57) ABSTRACT

A wavelength converter is disclosed. The converter comprises a broadband light source producing light having a plurality of wavelengths. Further, a semiconductor optical amplifier is provided that receives the light from the light source. The semiconductor optical amplifier amplifies the light under the control of a control signal related to an optical signal of a first wavelength. Next, a demultiplexer receives the output of the semiconductor optical amplifier and extracts from the amplified optical signal at least one of the plurality of wavelengths.

25 Claims, 18 Drawing Sheets

"ON"

"OFF"

WAVELENGTH CONVERTER USING BRAGG-GRATING

RELATED APPLICATIONS

"Priority is hereby claimed under 35 U.S.C. §120 to U.S. Provisional Patent Application Serial No. 60/348,927 filed Oct. 22, 2001, U.S. Provisional Patent Application No. 60/373,803 filed Apr. 19, 2002, and a continuation-in-part of U.S. patent application Ser. No. 10/104,273 filed Mar. 22, 2002, U.S. patent application Ser. No. 10/177,632 filed Jun. 19, 2002, U.S. patent application Ser. No. 10/188,955 filed Jul. 3, 2002, U.S. patent application Ser. No. 10/190,018 filed Jul. 5, 2002, and U.S. patent application Ser. No. 10/202,054 filed Jul. 23, 2002, each of which is incorporated by reference."

TECHNICAL FIELD

The present invention relates to wavelength converters, and more particularly, to a wavelength converter that utilizes a Bragg-grating.

BACKGROUND

Wavelength converters are often used in wavelength division multiplex (WDM) optical communications systems. A wavelength converter is a device that can convert data carried on a first wavelength of light into the same data carried onto a second wavelength of light. Early wavelength converters operated by extracting the data from the first wavelength by demodulation techniques and then re-modulating the data onto a second wavelength of light. This opto-electro-opto conversion process required relatively complex circuitry. More recent wavelength converters are all optical, i.e., the data is converted all in the optical domain using optical components. An example of this is shown in U.S. Pat. No. 6,356,382 to Nakano et al. Thus, there are various methods to perform the wavelength conversion function.

DETAILED DESCRIPTION

The present invention describes a method and apparatus for wavelength conversion in an optical telecommunications system. In the following description, numerous specific details are provided to provide a thorough understanding of the embodiments of the invention. One skilled in the relevant art will recognize, however, that the invention can be practiced without one or more of the specific details, or with other methods, components, etc. In other instances, well-known structures or operations are not shown or described in detail to avoid obscuring aspects of various embodiments of the invention.

Reference throughout the specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout the specification are not necessarily all referring to the same embodiment. Furthermore, the particular features, structures, or characteristics may be combined in any suitable manner in one or more embodiments.

Further, although the present invention is described in terms of a WDM system, the apparatus and method of the present invention can equally be applicable to any optical system that utilizes multiple frequencies. Thus, the description below is but one embodiment of the present invention.

Figure 1:
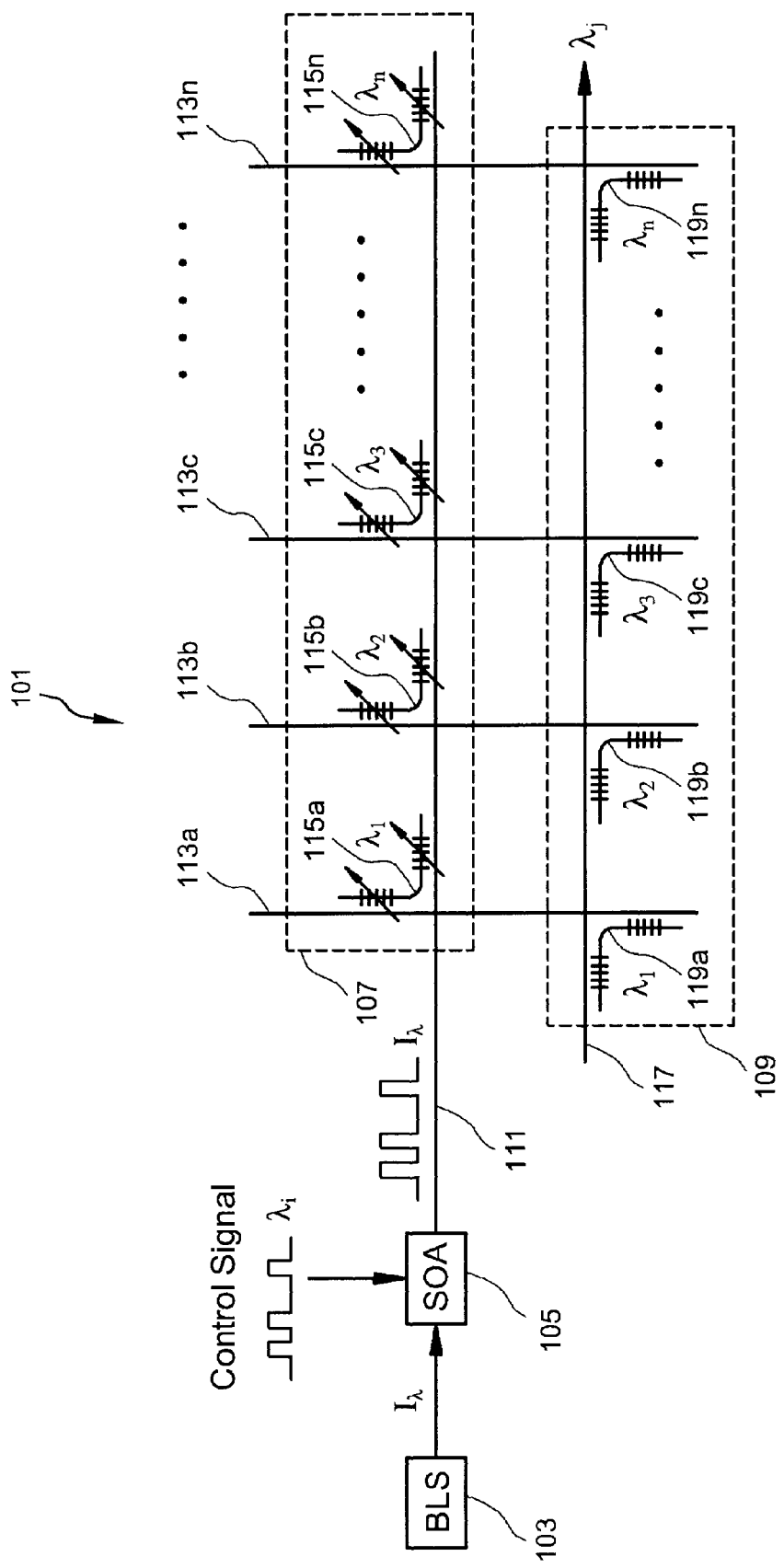
FIG. 1 is a schematic illustration of an embodiment of the present invention.

FIG. 1 illustrates a wavelength converter 101 formed in accordance with the present invention. The wavelength converter includes a broadband light source (BLS) 103, a semiconductor optical amplifier (SOA) 105, a wavelength selective de-multiplexer 107, and a multiplexer 109. The broadband light source 103 provides light across a spectrum of wavelengths, and more particularly, wavelengths within the band of interest. In one embodiment, the broadband light source 103 provides light in the range of 1520 to 1570 nanometers, also referred to as the "C-band".

The broadband light source 103 provides the broadband light as an input to the SOA 105. The SOA 105 is operative to receive the broadband light from the broadband light source 103 and amplify that broadband light in accordance with an input control signal. The input control signal may either be electrical or optical in nature. Typically, the input control signal is modulated with data. As will be seen in greater detail below, the input control signal is related to the optical signal having a first wavelength that is to be converted to the second wavelength. The output of the SOA 105 is thus broadband light that is amplified and modulated by the control signal. In other words, the output of the SOA 105 is broadband light modulated by the data carried by the optical signal of the first wavelength.

In many respects, SOA 105 is similar in construction to a conventional semiconductor laser in that it consists of a layer of semiconductor material (known as the active region), sandwiched in between other layers of semiconductors of a different composition. An electrical current (as the control signal) is passed through the device and serves to excite electrons in the active region. When photons travel through the active region, this will cause these electrons to lose some of their extra energy in the form of more photons that match the wavelength (or wavelengths) of the initial input. Therefore, an optical signal passing through the active region is amplified and is said to have experienced gain. Moreover, by varying the electrical current either in the amplitude for time domain, the optical signal can be modulated. Additionally, the semiconductor layers that sandwich the active region are designed to help guide the light through the device. This is achieved through a difference in refractive index from the active region, in much the same way as the refractive index differs between an optical fiber's core and its cladding help to guide light. The SOA 105 is commercially available from companies such as Alcatel, Kamelian, Opto Speed, and others.

In one embodiment, the SOA 105 is controlled by a control signal related to the data carried on the optical signal having the first wavelength. In some embodiments, the optical signal having the first wavelength of light is directly input to the SOA 105 to control the amplification effect. In other embodiments, the optical signal having the first wavelength is converted into an electrical signal or electrical pulses that are input into the SOA 105 to control amplification. In either embodiment, the amplification provided by the SOA 105 to the broadband light input is dependent upon (i.e., modulated by) the control signal.

The output of the SOA 105 is a modulated and amplified broadband signal ($I_\lambda$) that is input into the wavelength selective demultiplexer 107. The wavelength selective demultiplexer 107 includes an input waveguide 111 and a plurality of intersecting waveguides 113a–n. The intersecting waveguides 113a–n intersect with the input waveguide 111. Disposed at the intersections of the intersecting waveguides 113 and the input waveguide 111 are switches 115a–n. As seen in further detail below, the switches 115a–n are selectively capable (when activated) of redirecting light of a specific wavelength into the associated intersecting waveguide 113a–n. The switches 115 are Bragg-grating based switches and are of the type disclosed in our co-pending applications noted above and which are herein incorporated by reference in their entirety. However, a description is provided herein for completeness.

Figure 2A:
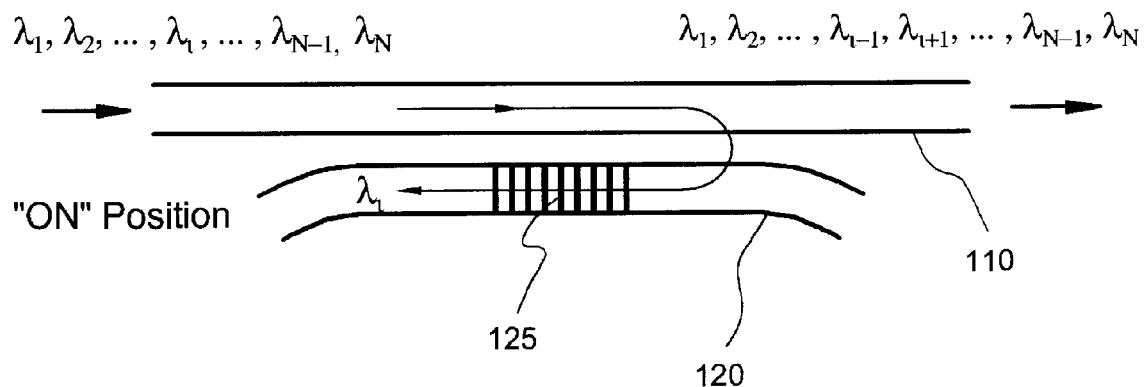
FIGS. 2A to 2F are schematic diagrams showing the on/off switching functions of a wavelength selective bridge waveguide of this invention.
Figure 2B:
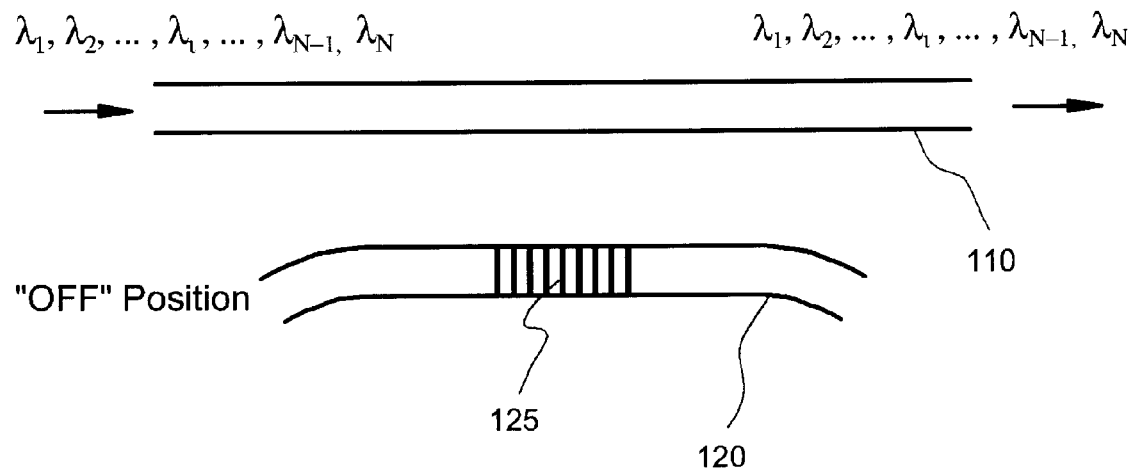

FIGS. 2A and 2B are schematic diagrams for showing the principles of operation of the switches 115. A multiplexed optical signal is transmitted in an optical waveguide 110 over N multiplexed wavelengths $\lambda_1, \lambda_2, \lambda_3, \ldots \lambda_N$ where N is a positive integer. This is a general characterization of a plurality of wavelengths carried by the waveguide 110. In the embodiment of FIG. 1, the waveguide 110 is equivalent to the input waveguide 111 and the optical signals $\lambda_1, \lambda_2, \lambda_3, \ldots, \lambda_N$ are equivalent to $I_\lambda$.

In FIG. 2A, a wavelength selective bridge waveguide 120 is moved to an on-position and coupled to the waveguide 110. An optical signal with a central wavelength $\lambda i$ particular to the Bragg gratings 125 disposed on the bridge waveguide 120 is guided into the wavelength selective bridge waveguide 120. The remaining wavelengths $\lambda_1, \lambda_2, \ldots, \lambda_{i-1}, \ldots, \lambda_{i+1}, \ldots, \lambda_N$ are not affected and continues to propagate over the waveguide 110. The Bragg gratings 125 have a specific pitch for reflecting the optical signal of the selected wavelength $\lambda_i$ onto the wavelength selective bridge waveguide 120.

In FIG. 2B, the wavelength selective bridge waveguide 120 is moved away from the waveguide 110 to a "bridge-off" position. There is no coupling between to the waveguide 110 and therefore no "detoured signal" entering into the bridge waveguide 120. The entire multiplexed signal over wavelengths $\lambda_1, \lambda_2, \lambda_3, \ldots, \lambda_N$ continue to propagate on the waveguide 110.

Figure 2C:
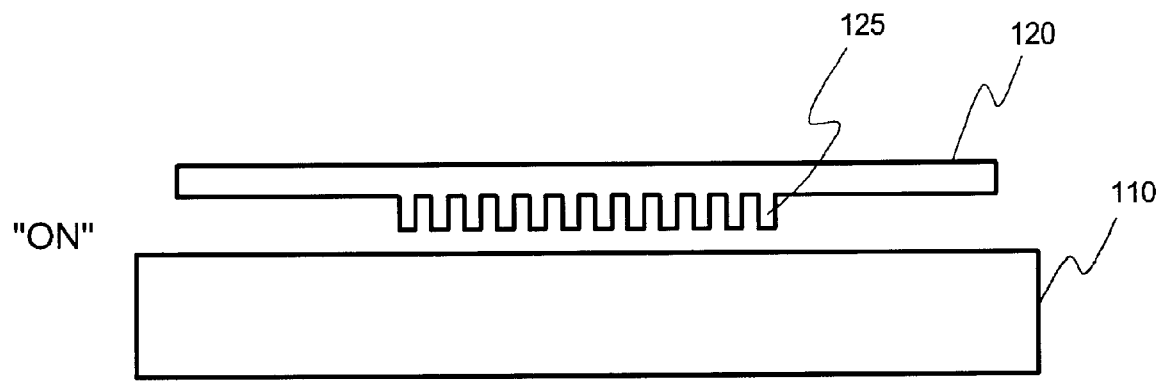
Figure 2D:
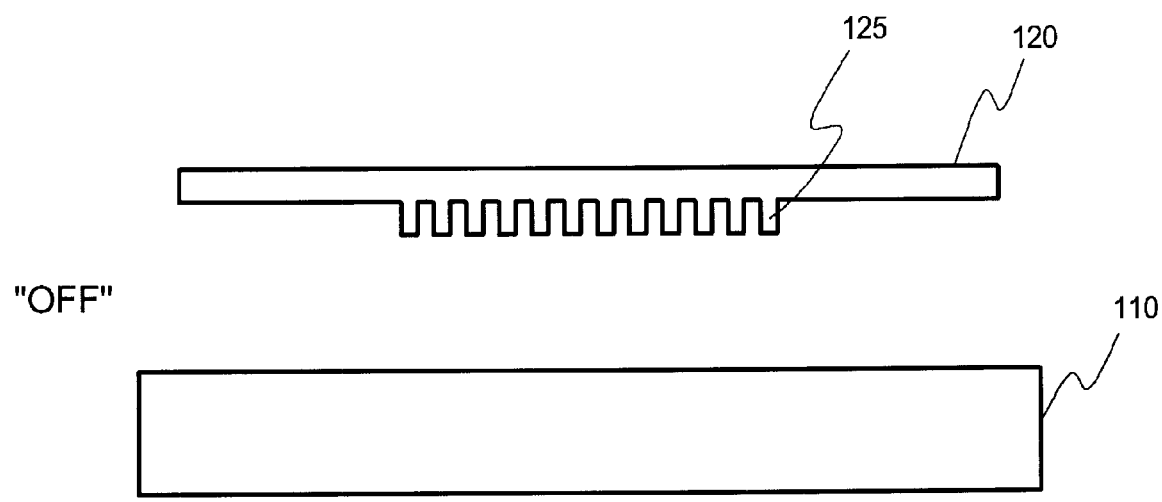
Figure 2E:
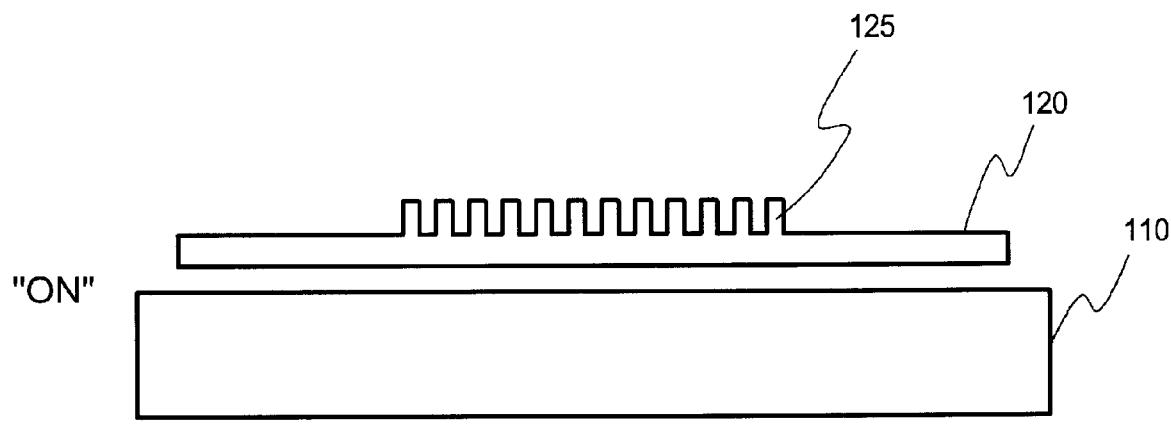
Figure 2F:
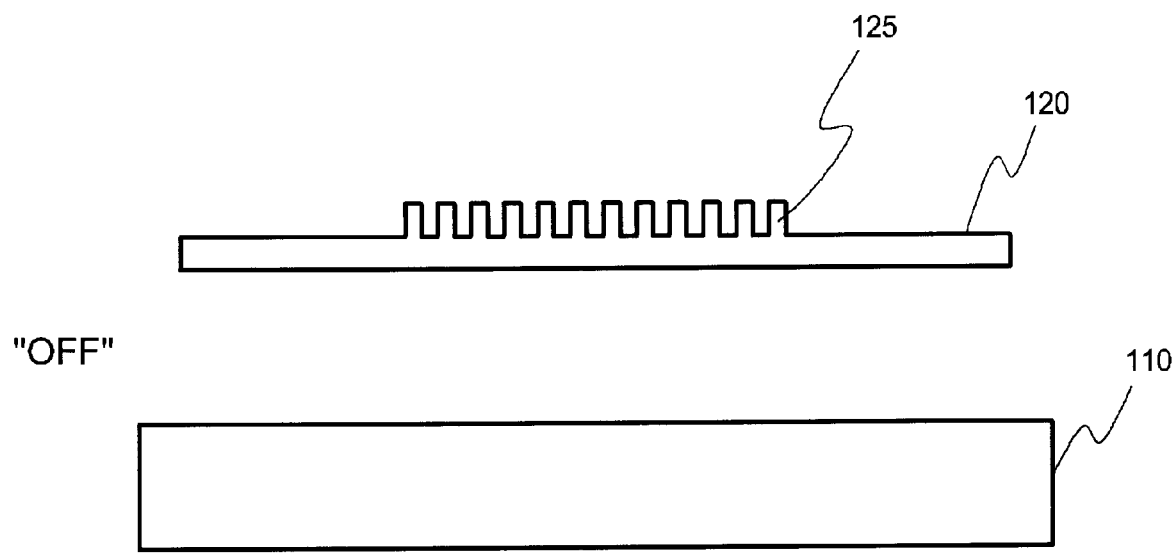

FIGS. 2C and 2D illustrate a detailed configuration of the Bragg-gratings formed on the wavelength selective bridge waveguide 120. The pitch between the gratings 125 defines a selected wavelength that will be reflected onto the bridge waveguide 120 when the wavelength selective bridge waveguide is at an on-position coupled to the waveguide 110 as that shown in FIG. 2A. Furthermore, as shown in FIGS. 2E and 2F, the Bragg-gratings 125 may be formed on a surface of the bridge waveguide 120 opposite the waveguide 110. Again, as the bridge waveguide 120 is moved to an "on" position coupled to the waveguide 110 in FIGS. 2C and 2E, an optical signal of a selected wavelength defined by the pitch between the Bragg gratings is coupled into the bridge waveguide 120. When the bridge waveguide 120 is moved to an "off" position in FIGS. 2D and 2F, the bridge waveguide 120 is completely decoupled and there is no "detoured signal" into the bridge waveguide 120.

Figure 3A:
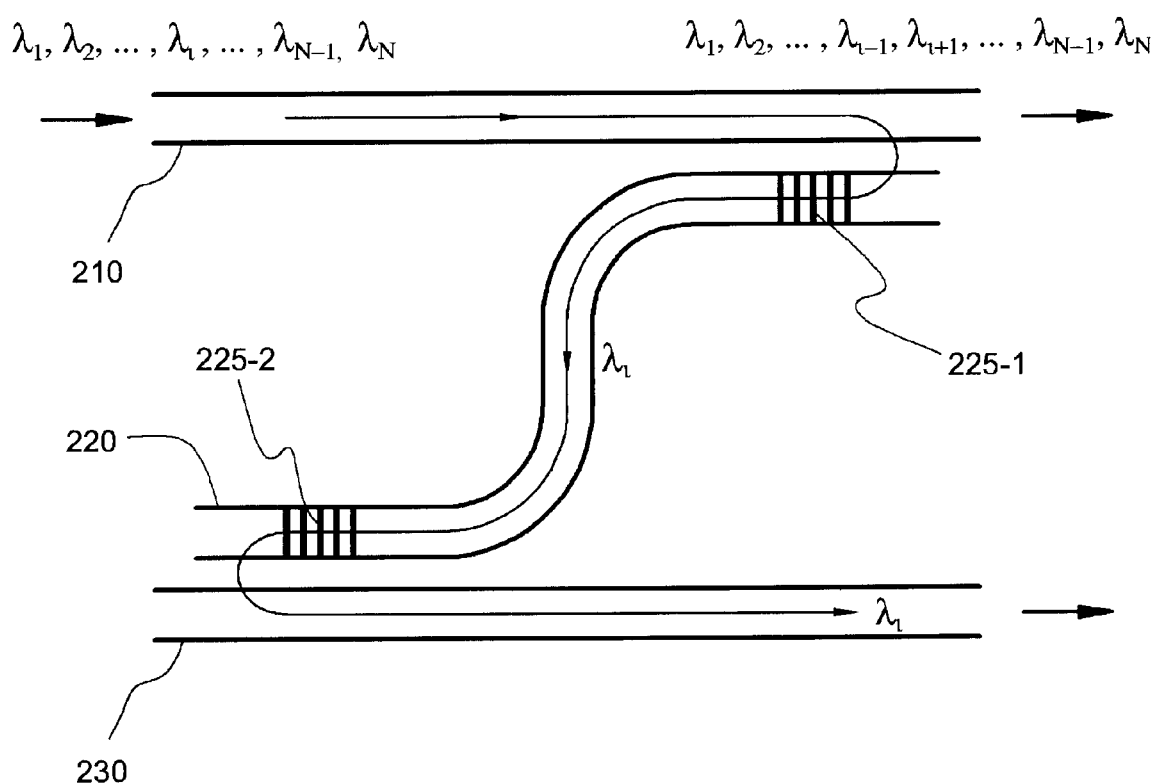
FIGS. 3A to 3B are cross sectional views for showing coupling configurations of a wavelength-selective bridge waveguide coupled between a waveguide and an outbound waveguide.

FIG. 3A shows a wavelength selective bridge waveguide 220 coupled between a bus waveguide 210 and a second waveguide 230. A multiplexed optical signal is transmitted in a bus waveguide 210 over N multiplexed wavelengths $\lambda_1, \lambda_2, \lambda_3, \ldots, \lambda_N$ where N is a positive integer. The wavelength selective bridge waveguide 220 has a first set of Bragg gratings disposed on a first "bridge on-ramp segment" 225-1 for coupling to the bus waveguide 210. An optical signal with a central wavelength $\lambda_i$ particular to the Bragg gratings 225 disposed on the bridge waveguide 220 is guided through the first bridge ramp segment 225-1 to be reflected into the wavelength selective bridge waveguide 220.

The remainder optical signals of the wavelengths $\lambda_1, \lambda_2, \lambda_3, \lambda_{i-1}, \ldots, \lambda_{i+1}, \ldots, \lambda_N$ are not affected and continues to transmit over the waveguide 210. The Bragg grating 225 has a specific pitch for reflecting the optical signal of the selected wavelength $\lambda_i$ onto the wavelength selective bridge waveguide 220. The wavelength selective bridge waveguide 220 further has a second set of Bragg gratings as a bridge off-ramp segment 225-2 coupled to an outbound waveguide 230. The second set of Bragg gratings has a same pitch as the first set of Bragg gratings. The selected wavelength $\lambda_i$ is guided through the bridge off-ramp segment 225-2 to be reflected and coupled into the outbound waveguide 230. The bridge waveguide 220 can be an optical fiber, waveguide or other optical transmission medium connected between the bridge on-ramp segment 225-1 and the bridge off-ramp segment 225-2.

Figure 3B:
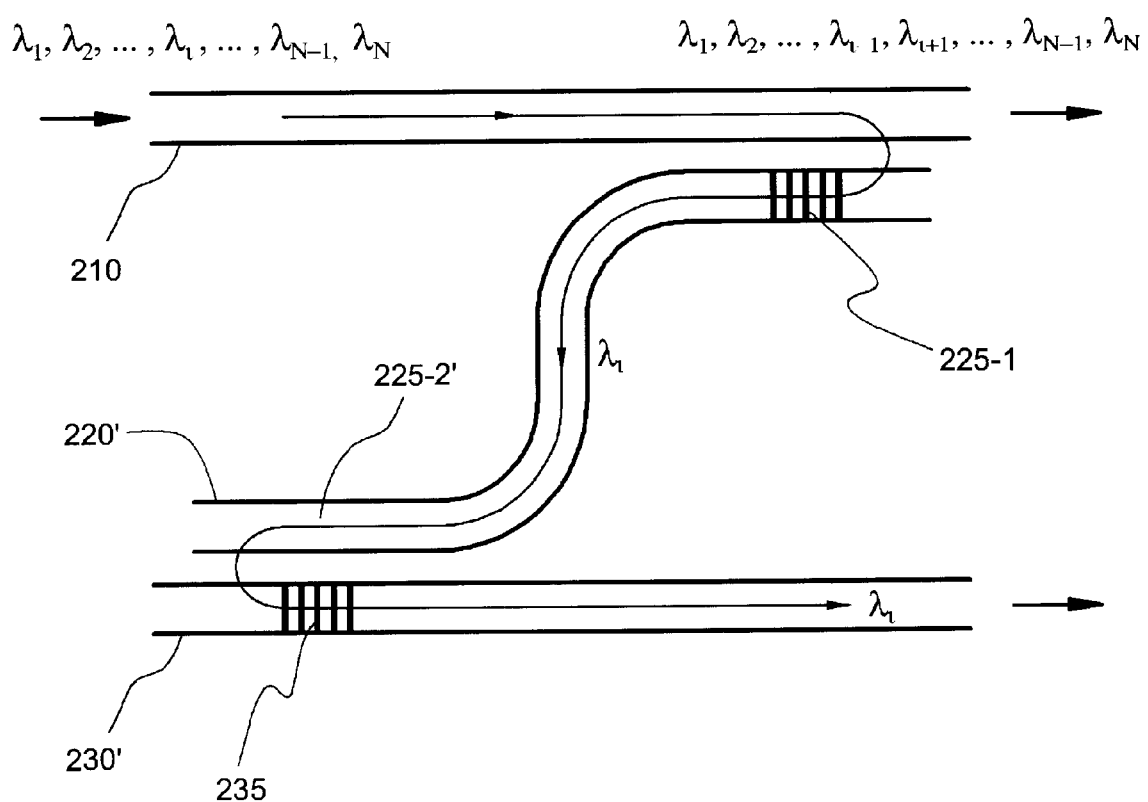

FIG. 3B shows another wavelength selective bridge waveguide 220' is coupled between a bus waveguide 210 and a second waveguide 230'. A multiplexed optical signal is transmitted in a bus waveguide 210 over N multiplexed wavelengths $\lambda_1, \lambda_2, \lambda_3, \ldots, \lambda_N$ where N is a positive integer.

The wavelength selective bridge waveguide 220' has a first set of Bragg gratings disposed on a first "bridge on-ramp segment" 225-1 for coupling to the bus waveguide 210. An optical signal with a central wavelength $\lambda_i$ particular to the Bragg gratings 225-1 disposed on the bridge waveguide 220' is guided through the first bridge ramp segment 225-1 to be reflected into the wavelength selective bridge waveguide 220'.

The remainder optical signals of the wavelengths $\lambda_1$, $\lambda_2$, $\lambda_3$, $\lambda_{i-1}$, $\lambda_{i+1}$, . . . , $\lambda_N$ are not affected and continues to transmit over the waveguide 210. The Bragg gratings 225-1 have a specific pitch for reflecting the optical signal of the selected wavelength $\lambda_i$ into the wavelength selective bridge waveguide 220'. The wavelength selective bridge waveguide 220' further has a bridge off-ramp segment 225-2' coupled to an outbound waveguide 230' near a section 235 of the outbound waveguide 230. The section 235 on the outbound waveguide 230' has a second set of Bragg gratings having a same pitch as the first set of Bragg gratings. The bridge waveguide 220 can be an optical fiber, waveguide or other optical transmission medium connected between the bridge on-ramp segment 225-1 and the bridge off-ramp segment 225-2'.

Figure 4A:
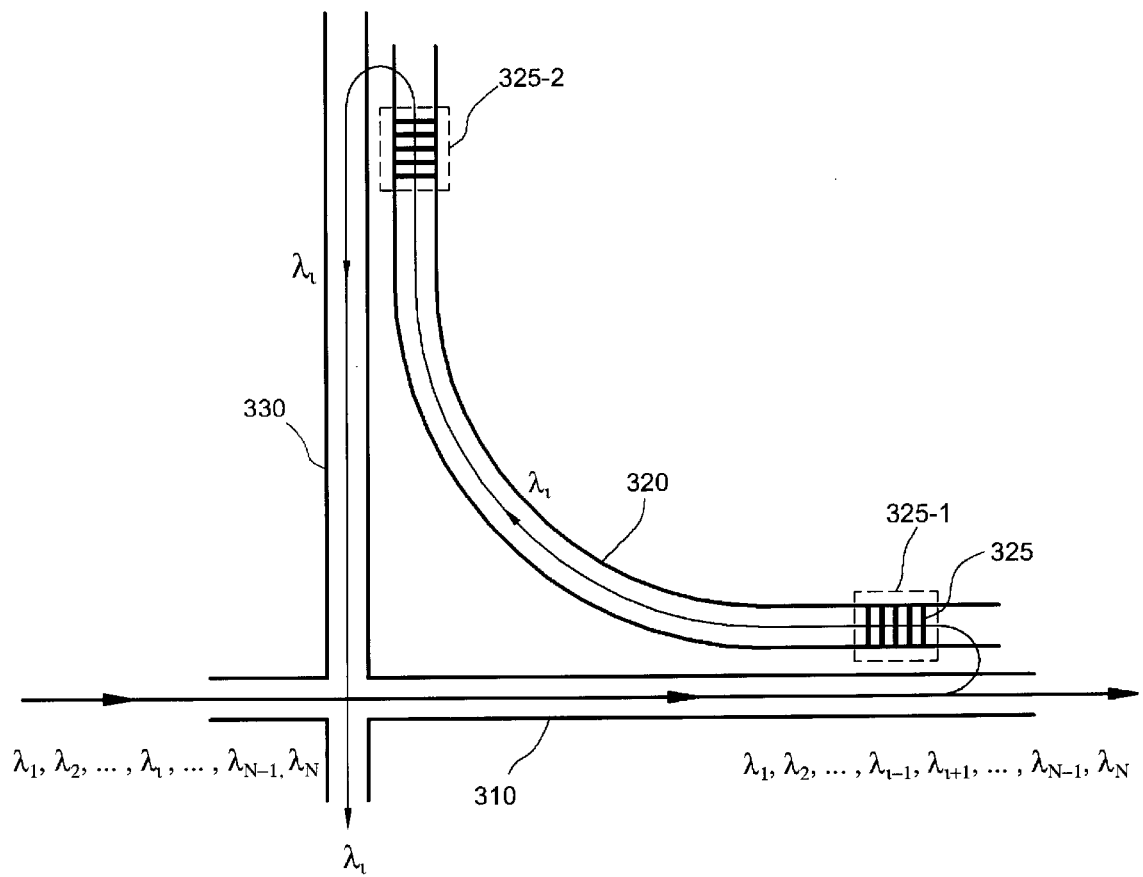
FIGS. 4A and 4B are functional diagrams for showing wavelength selective bridge waveguides acting as a switch that is coupled between the intersecting waveguides for switching and re-directing optical transmission of a selected wavelength.

FIG. 4A shows a wavelength selective bridge waveguide 320 is coupled between a bus waveguide 310 and an intersecting waveguide 330. Indeed, the following description shows the operation of the switches 115a–n at the intersection of the input waveguide 111 and the intersecting waveguides 11 3a–n. A multiplexed optical signal is transmitted in a bus waveguide 310 over N multiplexed wavelengths $\lambda_1$, $\lambda_2$, $\lambda_3$, . . . , $\lambda_N$ where N is a positive integer. The wavelength selective bridge waveguide 320 (also referred to as the switch 115 of FIG. 1) has a first set of Bragg gratings disposed on a first "bridge on-ramp segment" 325-1 for coupling to the bus waveguide 310. An optical signal with a central wavelength $\lambda_i$ particular to the Bragg gratings 325 disposed on the bridge waveguide 320 is guided through the first bridge ramp segment 325-1 to be reflected into the wavelength selective bridge waveguide 320. The remainder optical signals of the wavelengths $\lambda_1$, $\lambda_2$, $\lambda_3$, . . . , $\lambda_{i-1}$, $\lambda_{i+1}$, . . . , $\lambda_N$ are not affected and continues to propagate over the waveguide 310.

The Bragg gratings 325 have a specific pitch for reflecting the optical signal of the selected wavelength $\lambda_i$ into the wavelength selective bridge waveguide 320. The wavelength selective bridge waveguide 320 further has a second set of Bragg gratings 325 as a bridge off-ramp segment 325-2 coupled to an outbound waveguide 330. The bridge waveguide 320 can be an optical fiber, waveguide or other optical transmission medium connected between the bridge on-ramp segment and the bridge off-ramp segment 325-2.

Figure 4B:
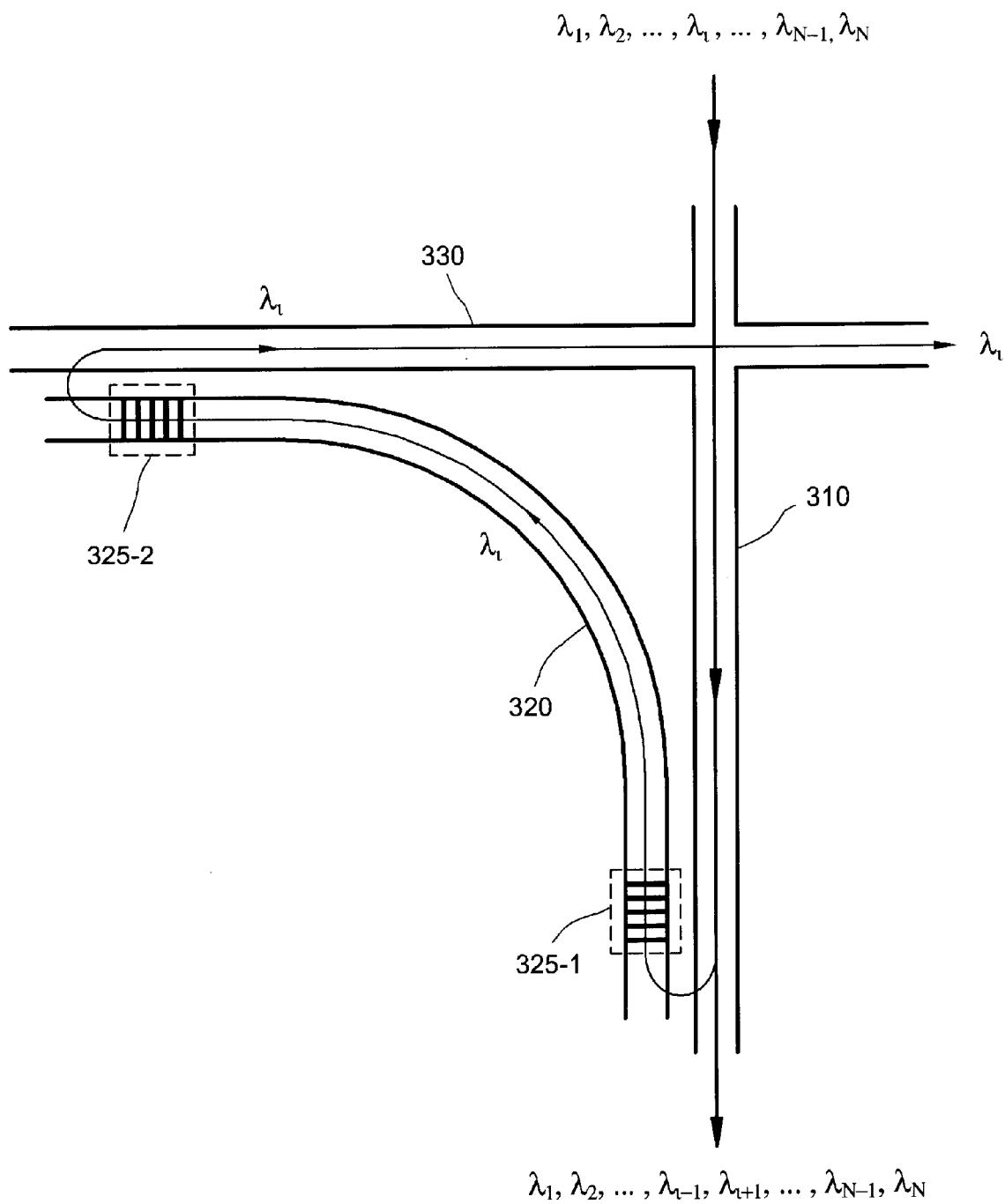

FIG. 4B is another embodiment with the bus waveguide 310 disposed in a vertical direction and an interesting outbound waveguide 330 disposed along a horizontal direction. As will be seen below, this embodiment of the switch is used in the non-movable bridge waveguide 109.

Figure 5A:
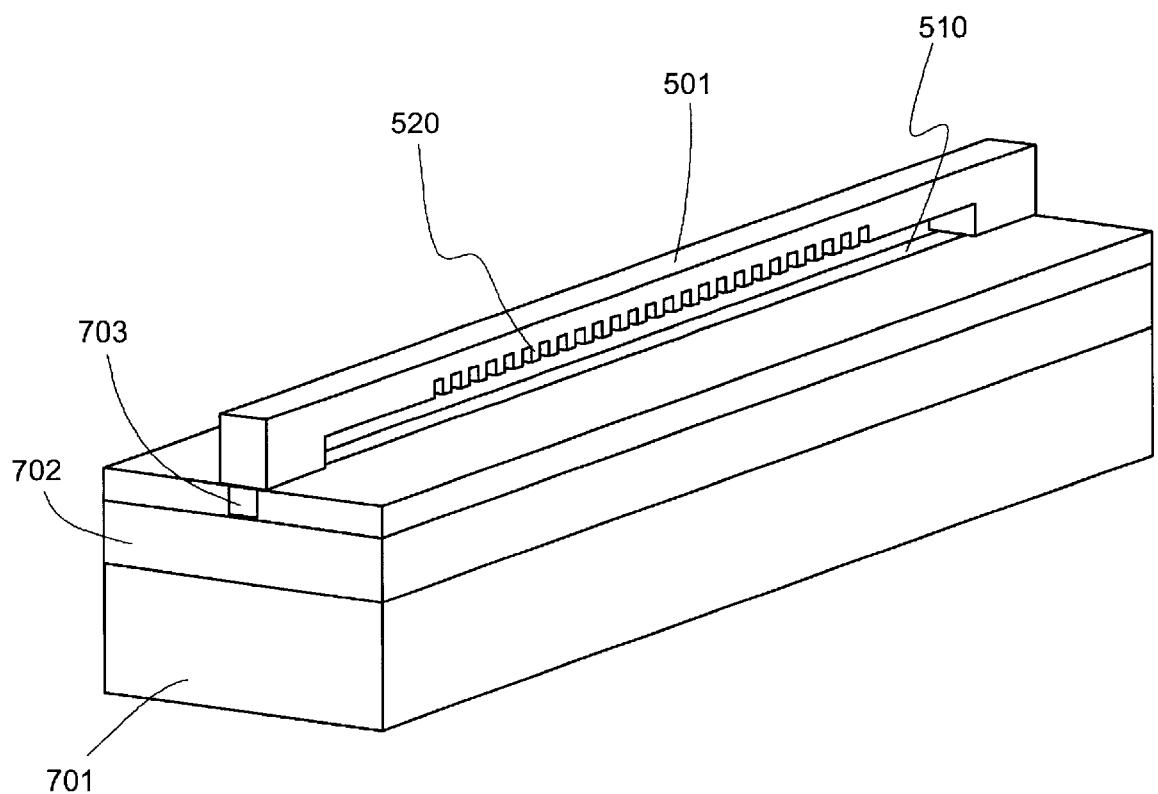
FIG. 5A illustrates a bridge-beam type switch with integrated Bragg grating element.

The structures shown in FIGS. 2–4 can be implemented as MEMS devices. For example, FIG. 5A depicts an illustrative embodiment of bridge-beam type switchable grating structure with integrated Bragg grating elements. The structure is fabricated using MEMS technology and semiconductor processing described below. On the substrate 701, a cladding layer 702 is formed first. Then the core layer 703 is deposited and patterned to form waveguide core that is shown more clearly in the cross-sectional view FIG. 5B. The bridge beam 501 is a waveguide consisting of integrated Bragg gratings 520 and an embedded electrode. When this waveguide, called a bridge waveguide, is electrostatically bent close enough to a waveguide 510, the wavelength that meets the Bragg phase-matching condition is coupled into the bridge waveguide. Through the bridge waveguide, the selected wavelength can then be directed into a desired output waveguide.

Figure 5B:
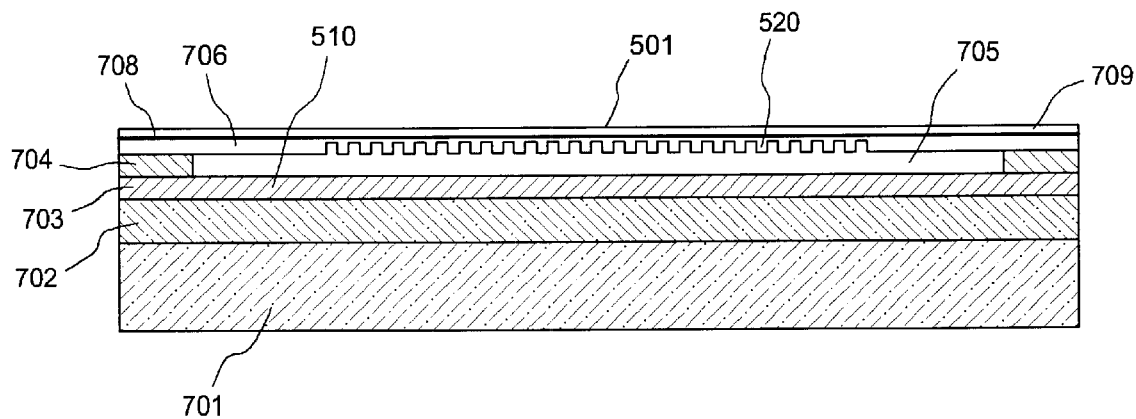
FIG. 5B illustrates the cross-sectional structure of a bridge-beam type switch in which the grating coupling is normally off.
Figure 5C:
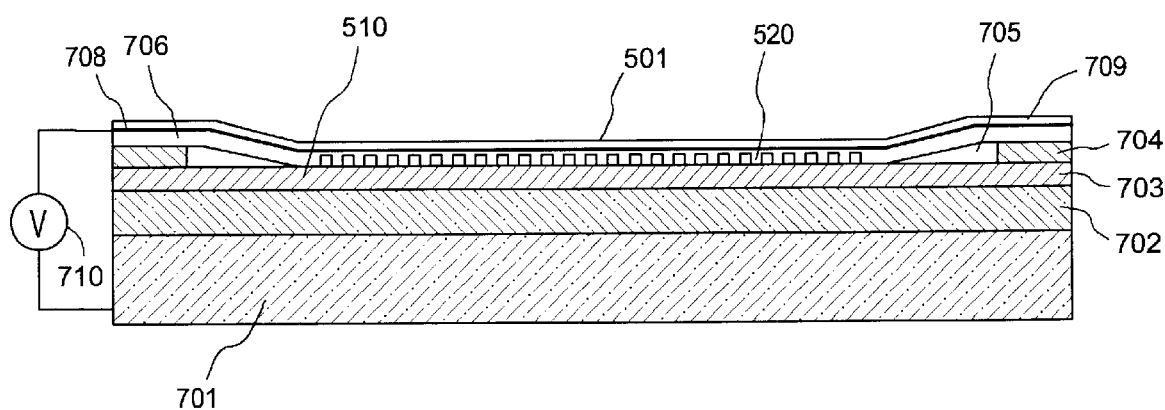
FIG. 5C shows the grating element of a bridge-beam type switch in the "on" position.

FIG. 5B shows the cross-sectional view of bridge-beam type switchable grating structure with integrated Bragg grating elements. After the cladding layer 702 and core layer 703 are deposited, a sacrificial layer is deposited after another cladding layer 704 is deposited and patterned. After the sacrificial layer is patterned and the grating grooves are etched on sacrificial layer, another cladding layer 706 is deposited. The electrode layer 708 and the insulation layer 709 are deposited subsequently. The etching process starts from layer 709 through into layer 704 after patterning. Finally the sacrificial layer is etched to form the air gap 705 between waveguide 510 and grating element 520. In an alternative way, the waveguide and the grating element can be fabricated on its own substrate first. Then they are aligned and bonded together to make the same structure shown in FIG. 7B. Due to the existence of air gap 705, the grating is off when the grating element is at normal position (no-voltages applied). Referring to FIG. 5C, when an appropriate voltage 710 is applied between the electrode 708 and substrate 701, the grating element 520 is deflected toward waveguide 510 by the electrostatic force. The grating is turned "on" when the grating element 520 moving close enough to input waveguide 510.

Figure 6A:
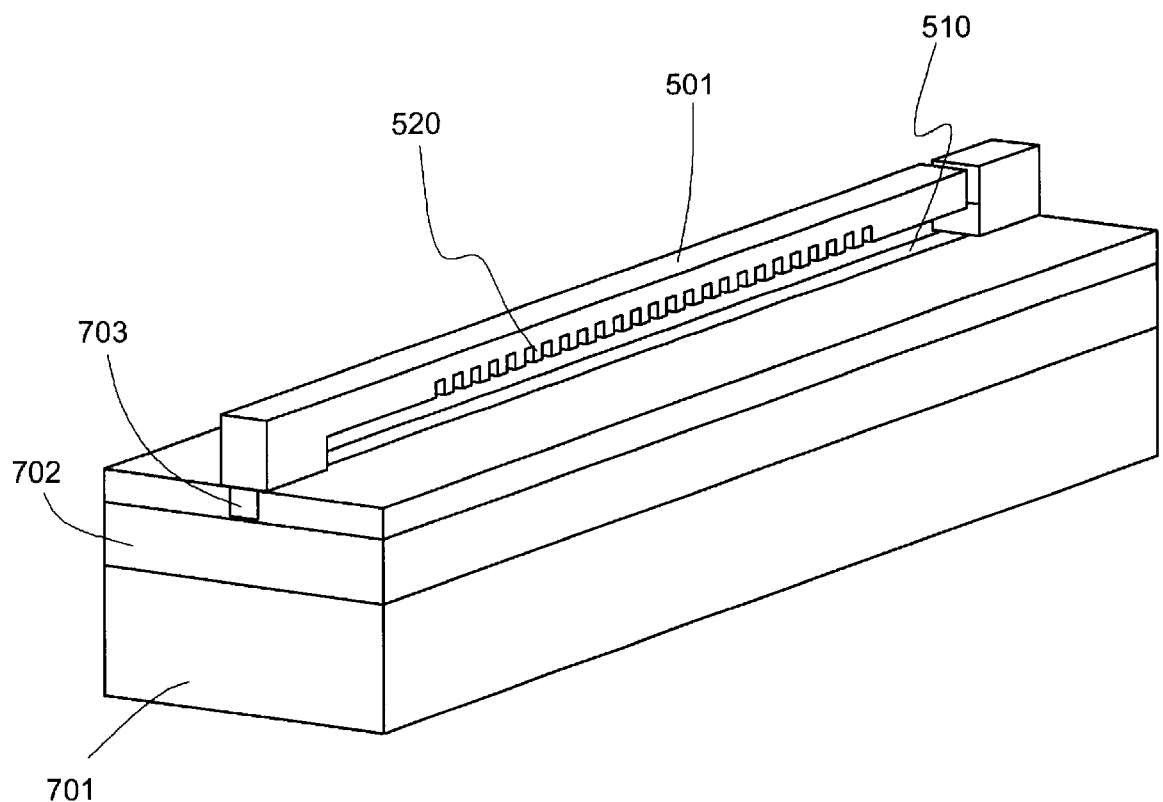
FIG. 6A illustrates a cantilever-beam type switch with integrated Bragg grating element.
Figure 6B:
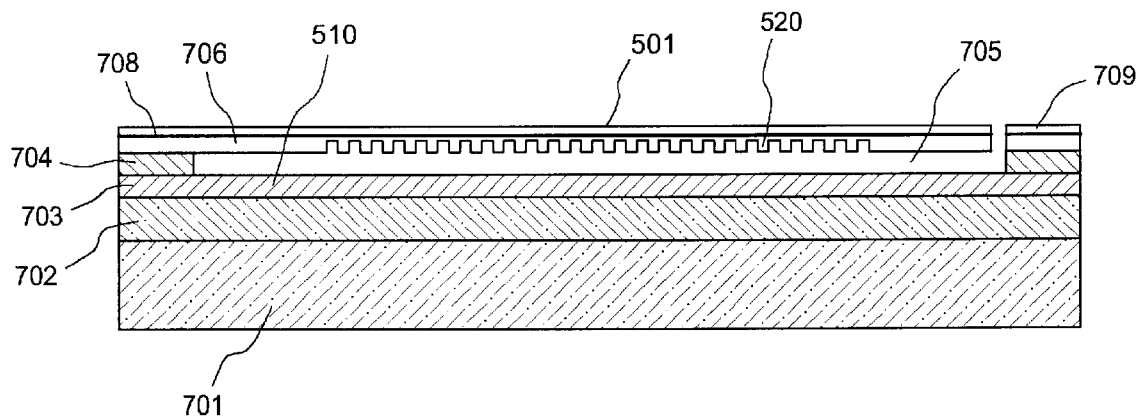
FIG. 6B illustrates the cross-sectional structure of a cantilever-beam type switch in which the grating coupling is normally off.
Figure 6C:
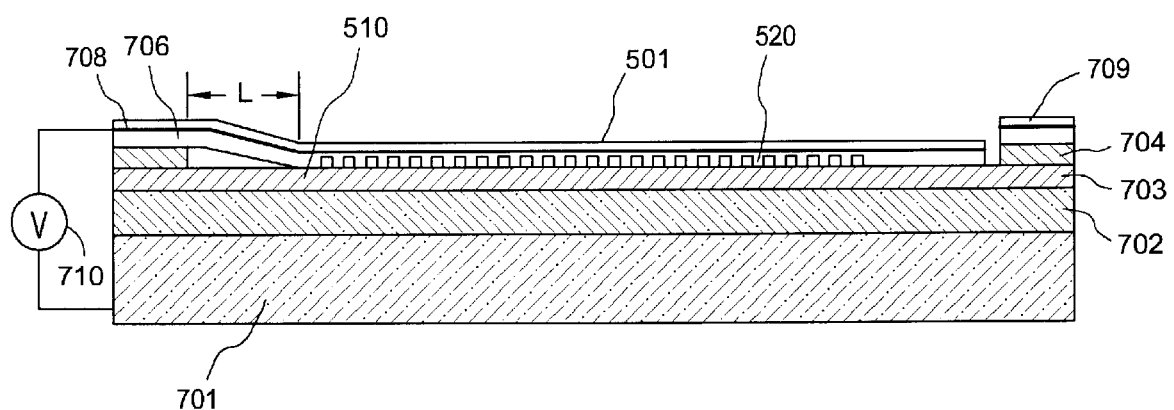
FIG. 6C shows the grating element of a cantilever-beam type switch in the "on" position.

FIG. 6A depicts an illustrative embodiment of cantilever-beam type switchable grating structure with integrated Bragg grating elements. The structure is fabricated using similar MEMS technology and semiconductor processing described above. In this arrangement, the stress and strain in the grating segment 520 can be reduced greatly. Therefore, the lifetime of grating element can be improved. FIG. 6B shows the cross-sectional structure of a cantilever-beam type switch. Referring to FIG. 6C, the cantilever beam 501 is deflected by the electrostatic force. Applying voltages 710 between substrate 701 and electrode 708 controls the electrostatic force applied to the cantilever beam 501. Therefore, by controlling the applying voltages 710 the wavelength-selective optical function can be activated through varying the degree of coupling between Bragg grating 520 and input waveguide 510.

An adequate beam length L is required in order to deflect the beam 501 to certain displacement within the elastic range of the material. For example, a 500 um long cantilever Si beam with the section of 12 um×3 um can be easily deformed by 4 um at the tip of the beam. Another major advantage for the cantilever beam structure is that the movable beam 501 can be shorter and therefore reduce the size of the switch.

Figure 7A:
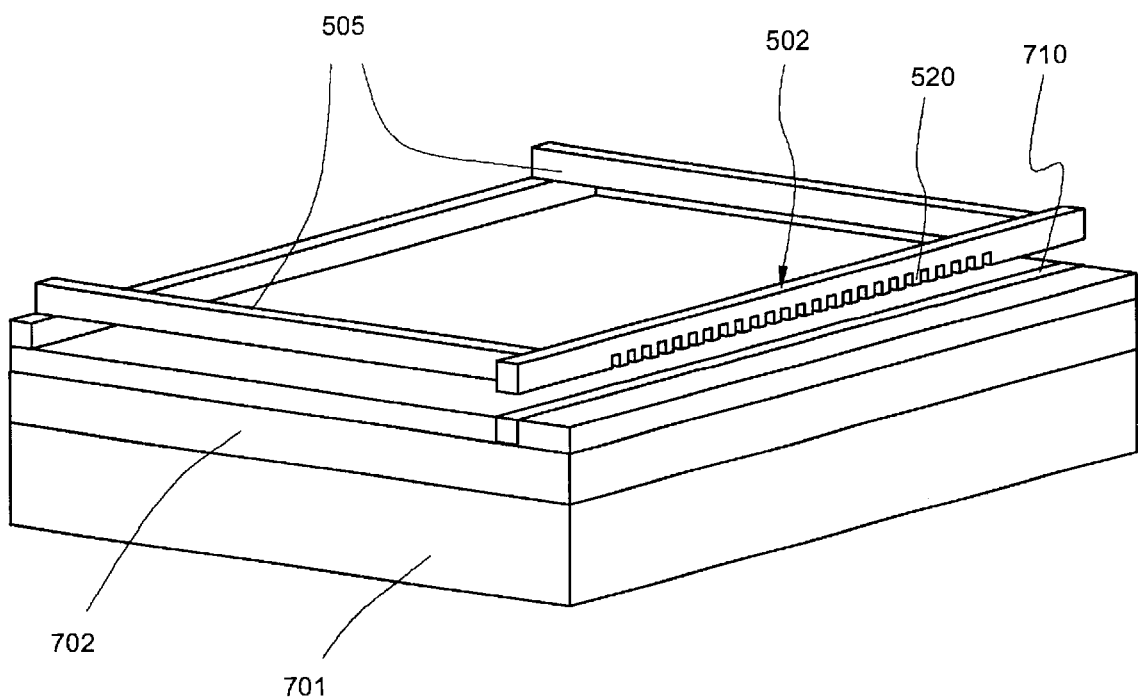
FIG. 7A illustrates a dual cantilever-beam type switch with integrated Bragg grating element.
Figure 7B:
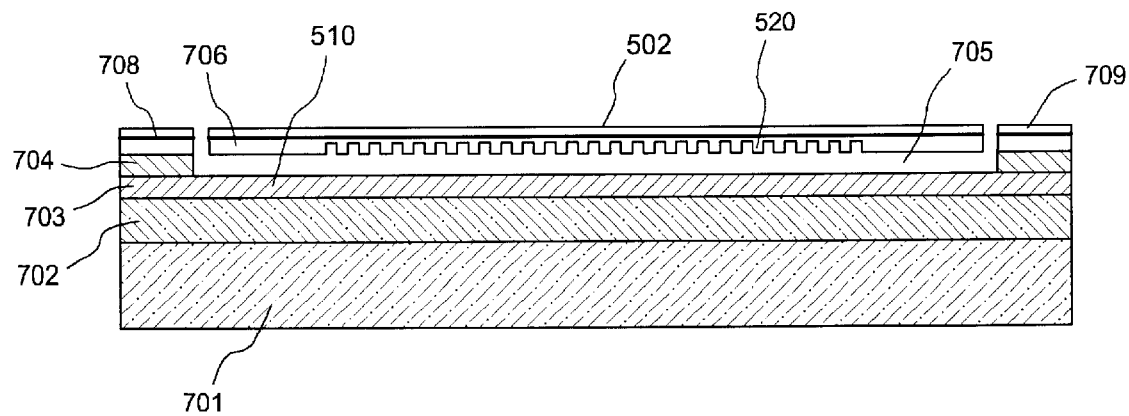
FIG. 7B illustrates the cross-sectional structure of a dual cantilever-beam type switch in which the grating coupling is normally off.
Figure 7C:
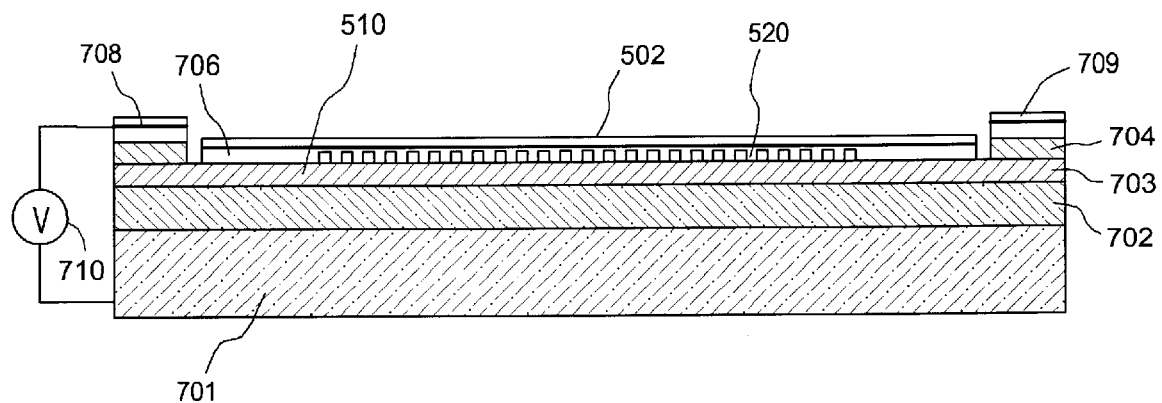
FIG. 7C shows the grating element of a dual cantilever-beam type switch in the "on" position.

FIG. 7A illustrates another embodiment of the switch. This is a dual cantilever-beam type switch. In this structure the grating element is fabricated on a movable beam 502, which is supported by two cantilever beams 505. In this arrangement, the stress and strain in the grating segment can be eliminated almost completely if the electrode pattern is also located appropriately. Another advantage is that the material of cantilever beams 505 does not necessarily have to be the same as the material of grating element 520. For instance, cantilever beams 505 can be made of metal to improve the elasticity of the beams. In addition, the anchor structure can be in different forms, e.g., MEMS springs or hinges. Therefore, a large displacement and smaller sized grating element is more achievable in this structure. FIGS. 7B and 7C shows the cross-sectional structure of a dual cantilever-beam type switch. Similar to the operations described above, the grating element 520 is moved towards the waveguide 510 by applying voltages 710 to electrode 708 and substrate 701.

Figure 8:
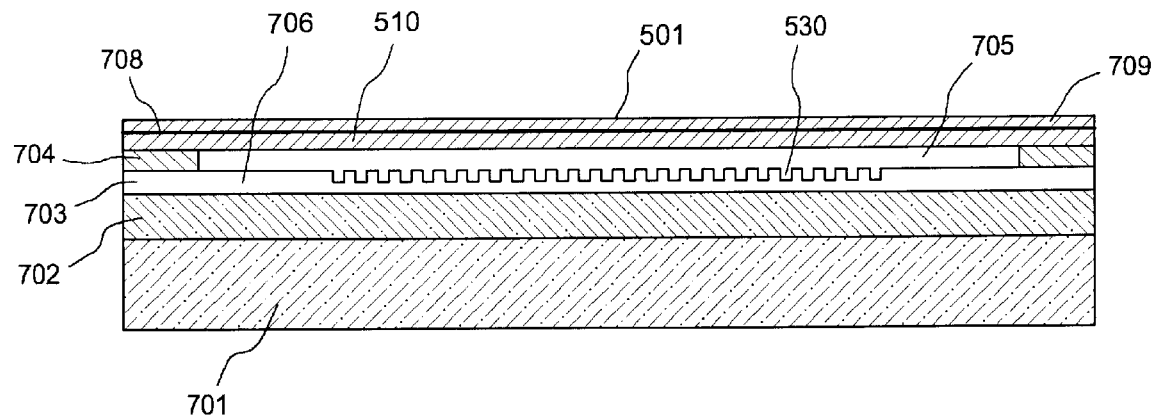
FIG. 8 illustrates the cross-sectional structure of another embodiment of the grating element.

FIG. 8 shows an alternate structure of the grating where the grating is located on the bottom side, or the surface side of the substrate. The structure can be fabricated by applying semiconductor processing technology to form the Bragg gratings 530 on the core layer 703 while positioning the movable beam 501 and the Bragg gratings 530 to have a small gap 705 from the waveguide 510. Similar to the operations described above, an electric conductive layer 708 is formed on the movable beam 501 for applying the voltage to assert an electrostatic force to bend the movable beam 501. The electrostatic force thus activates the movable switch by coupling a waveguide 706 to waveguide 510. The Bragg gratings 530 thus carry out a wavelength-selective optical switch function.

Figure 9:
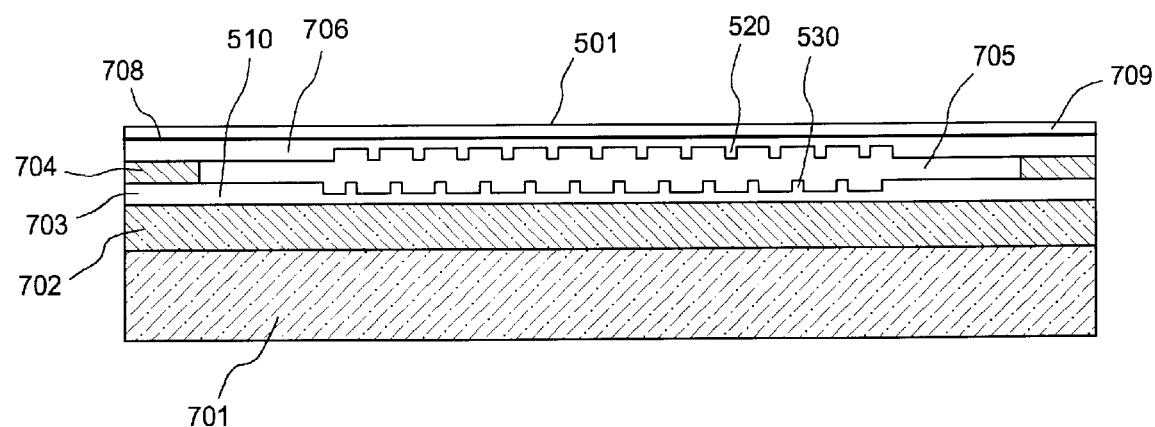
FIG. 9 illustrates an embodiment where the grating elements are fabricated on both the substrate and the movable beam.

FIG. 9 is also another alternate structure of switchable gratings. In this structure the grating is located on both top and bottom sides. Similar semiconductor processing technology can be used to form the Bragg gratings 520 on the movable beam 501 and the Bragg gratings 530 on the waveguide 510. A small gap is formed between waveguides 510 and 706. An electric conductive layer 708 is also formed on the movable beam 501 for applying the voltage to assert an electrostatic force to bend the movable beam 501. Similar to the operations described above, the electrostatic force thus activates the switch by coupling the selected wavelength from waveguide 510 to waveguide 706.

Figure 10:
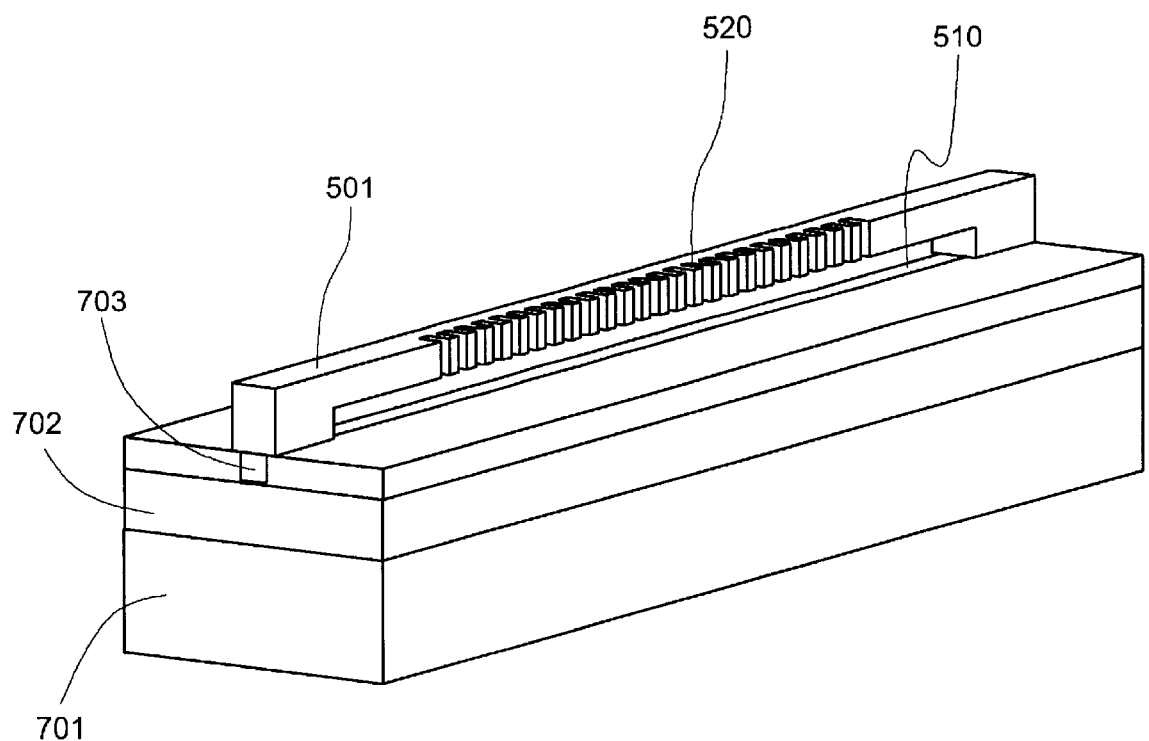
FIG. 10 illustrates an embodiment where the grating elements are fabricated on the horizontal sides of the movable beam.

In the structures described above, the grating element is located faced up or down to the substrate. However, the grating element can also fabricated on the sides of the waveguide, as illustrated in FIG. 10. In this embodiment, the gratings 520 are fabricated on the horizontal sides of the movable beam 501 and the rest of the structure are similar to those structure described above and all the wavelength-selective functions and operations are also similar to those described above. In addition, by rearranging the pattern of the electrode, the grating structure can also be made on the top side of the cantilever or bridge beams. This structure may provide a cost advantage in manufacturing.

Figure 11A:
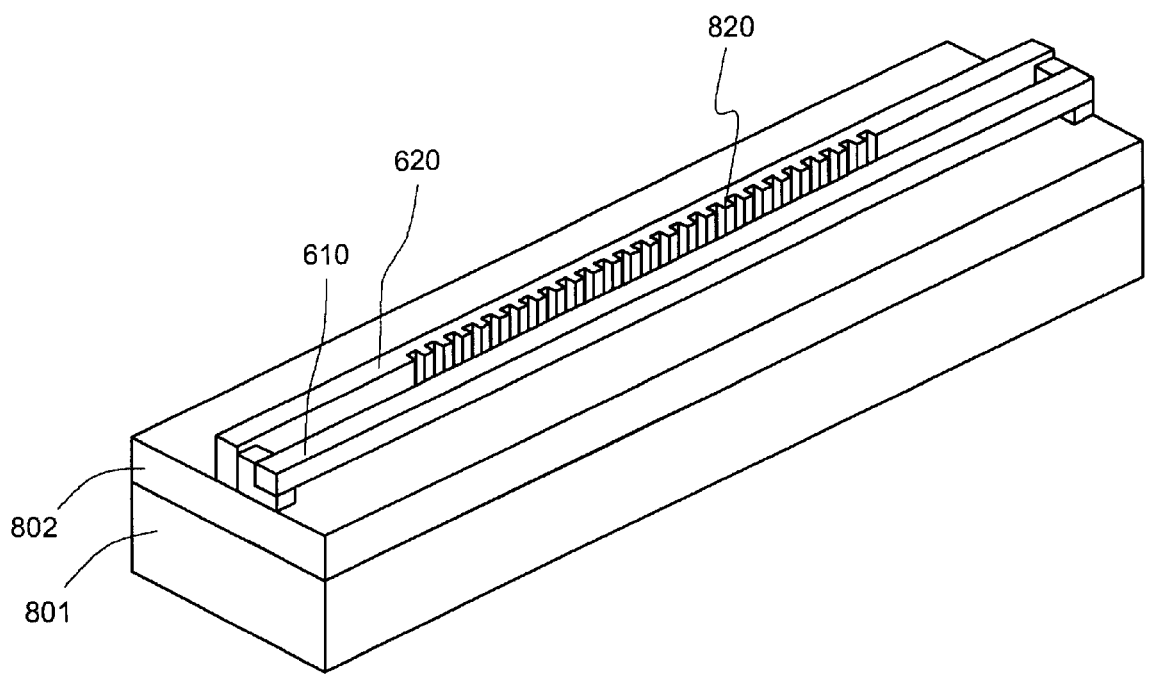
FIGS. 11A and 11B illustrate a grating element where the waveguides are both fabricated on the same surface of the substrate.
Figure 11B:
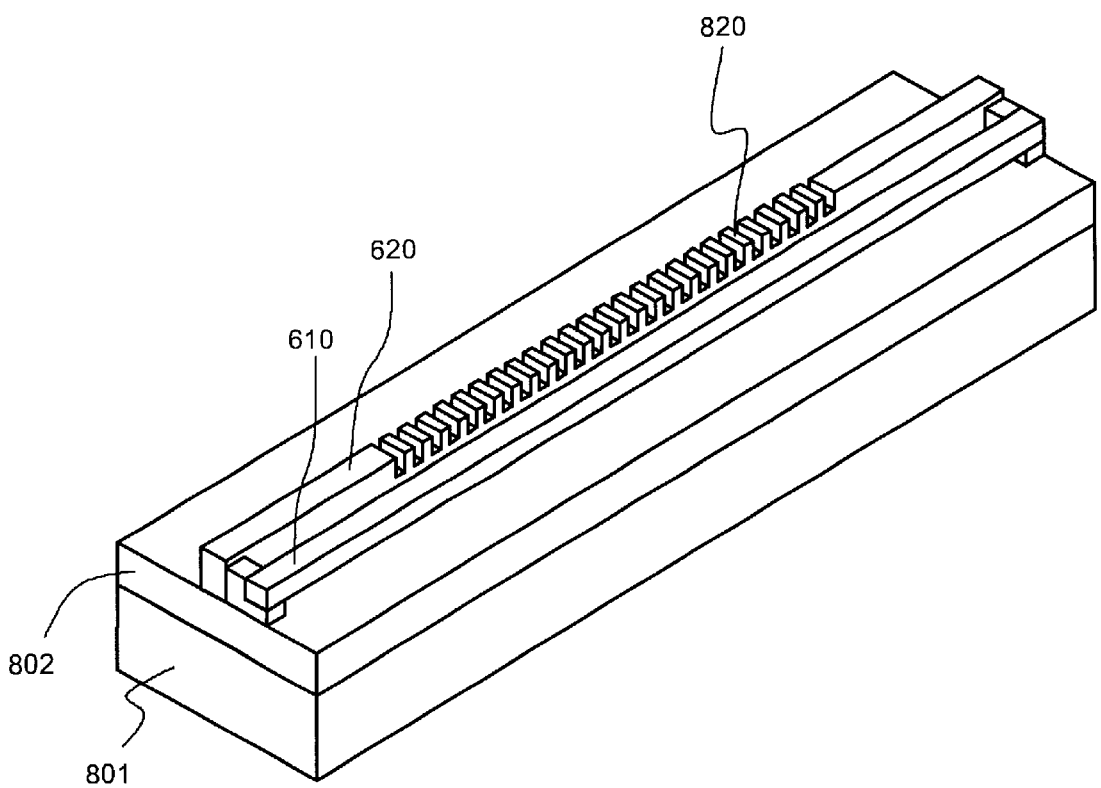

FIG. 11A shows another structure of switchable gratings. Instead of arranging the coupling waveguides as several vertical layers supported on a semiconductor substrate as shown above, the coupling waveguides 610 and 620 are formed as co-planar on a same cladding layer 802, supported on a semiconductor substrate 801. The movable waveguide 610 and coupling waveguide 620 have their own embedded electrodes, similar to those described above. Again, the Bragg gratings 820 can be formed on one or both of the waveguides 610 and 620 as described above. When electrostatic voltages are applied between these electrodes, movable waveguide 610 is moved towards waveguide 620 and thus activate the optical switch. FIG. 11B shows another structure with the gratings 820 facing upward.

Returning to FIG. 1, thus, each of the switches 115a–n extract from the input waveguide 111 one of the frequencies ($\lambda_1$–$\lambda_n$) contained in the broadband signal output by the SOA 105. In FIG. 1, it can be seen that the intersecting waveguide 113a contains the optical signal carried by$\lambda_1$. Similarly, the intersecting waveguide 113b carries the signal carried by wavelength$\lambda_2$. Intersecting waveguide 113c carries the signal carried on wavelength $\lambda_3$. Finally, intersecting waveguide 113n carries the signal carried on wavelength$\lambda_n$. It should be noted that the switches 115a–n in the wavelength selective demultiplexer 107 are selectively activated as desired. Thus, the switch 115a may be activated to switch the signal carried on wavelength$\lambda_1$ to the intersecting waveguide 113a. Alternatively, the switch 115a may be deactivated such that the intersecting waveguide 113a does not carry the signal on wavelength $\lambda_1$. In that situation, the input waveguide 111 continues to carry the signal on wavelength $\lambda_1$. Thus, the wavelength selective demultiplexer 107 can selectively extract one or more wavelengths from the broadband input to one or more intersecting waveguides 113a–n.

The intersecting waveguides 113a–113n are all input into the multiplexer 109. Once input into the multiplexer 109, the intersecting waveguides 113a–113n further intersect an output waveguide 117. Located at the intersection of the intersecting waveguides 113a–113n with the output waveguide 117 are switches 119a–119n. These switches, in one embodiment, are fixed and operate to redirect the signal carried on the intersecting waveguides 113a–113n into the output waveguide 117. In an alternative embodiment, the switches 11 9a–119n may also be selectively activated to provide another configurable option to the user. The switches 119a–119n are similar to that of the switches 115a–115n.

As seen, an input signal having wavelength $\lambda_i$ can be provided to the wavelength converter 101 of the present invention and be converted into an arbitrary wavelength that is output by the output waveguide 117. The arbitrary wavelength may be selected from the wavelengths provided by the broadband light source 103. By selectively controlling the switches 115a–115n, one or more output wavelengths having the same data carried by the optical signal having the input wavelength $\lambda_i$ can be output. In this manner, a wavelength converter is implemented.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

We claim:

1. A wavelength converter comprising:
   a broadband light source producing light having a plurality of wavelengths;
   a semiconductor optical amplifier that receives said light having a plurality of wavelengths, said semiconductor optical amplifier amplifying said light under the control of a control signal and producing an amplified optical signal; and
   a demultiplexer that receives the output of said semiconductor optical amplifier and extracts from said amplified optical signal at least one of said plurality of wavelengths as an output optical signal at a second wavelength,
   wherein said demultiplexer comprises:
   (1) an input waveguide for carrying the output of said semiconductor optical amplifier;
   (2) a plurality of intersecting waveguides intersecting with said input waveguide to form a plurality of intersections; and
   (3) a plurality of switches disposed on said plurality of intersections.

2. The wavelength converter of claim 1 wherein said control signal is derived from an input optical signal of a first wavelength.

3. The wavelength converter of claim 1 wherein said broadband light source provides light in the range of 1520 to 1570 nanometers.

4. The wavelength converter of claim 1 further including a multiplexer for routing said output optical signal into an output waveguide.

5. The wavelength converter of claim 1 wherein said plurality of switches disposed on said plurality of intersections selectively switches one of said plurality of wavelengths into an associated intersecting waveguide and for selectively transmitting the remaining ones of said plurality of wavelengths.

6. The wavelength converter of claim 1 wherein said switches comprise Bragg gratings that have a periodicity suitable for switching one of said plurality of wavelengths from said input waveguide into an associated one of said intersecting waveguides.

7. The wavelength converter of claim 1 wherein said switches can be engaged or disengaged to said input waveguide and an associated one of said intersecting waveguides.

8. The wavelength converter of claim 1 wherein said demultiplexer comprises:
   an input waveguide for carrying the output of said semiconductor optical amplifier,
   an intersecting waveguide disposed proximal to said input waveguide, said intersecting waveguide or said input waveguide having a Bragg grating formed thereon, said input waveguide and said intersecting waveguide separated by a gap distance when in an off state; and
   means for displacing said Bragg grating sufficiently towards said input waveguide when in an on state such that said Bragg grating can selectively extract one of said plurality of wavelengths.

9. The wavelength converter of claim 8 wherein said Bragg grating has a periodicity suitable for filtering said one of said plurality of wavelengths into said intersecting waveguide.

10. The wavelength converter of claim 8 wherein said means for displacing comprises an electrically controllable microelectromechanical system (MEMS).

11. The wavelength converter of claim 8 wherein said means for displacing is an electrostatic moving means for moving said Bragg grating for activating said Bragg grating.

12. A method for converting a first optical signal having a first wavelength to a second optical signal having a second wavelength comprising:
   providing a broadband light source that outputs light having a plurality of wavelengths;
   amplifyng said light using an amplification means, said amplification means being controlled by a control signal related to said first optical signal and to produce an amplified optical signal; and
   demultiplexing said amplified optical signal to extract said second optical signal, wherein said demultiplexing is performed by a demultiplexer comprising:
   (1) an input waveguide for carrying the amplified output signal of said amplification means;
   (2) a plurality of intersecting waveguides intersecting with said input waveguide to form a plurality of intersections; and
   (3) a plurality of switches disposed on said plurality of intersections.

13. The method of claim 12 wherein said broadband light source provides light in the range of 1520 to 1570 nanometers.

14. The method of claim 12 further including multiplexing said second optical signal into an output waveguide.

15. The method of claim 12 wherein said plurality of switches disposed on said plurality of intersections selectively switches one of said plurality of wavelengths into an associated intersecting waveguide and for selectively transmitting the remaining ones of said plurality of wavelengths.

16. The method of claim 12 wherein said plurality of switches comprise Bragg gratings that have a periodicity suitable for switching one of said plurality of wavelengths from said input waveguide into an associated one of said intersecting waveguides.

17. The method of claim 12 wherein said plurality of switches can be engaged or disengaged to said input waveguide and an associated one of said intersecting waveguides.

18. The method of claim 12 wherein said demultiplexing comprises:
   placing said amplified output signal into an input waveguide;
   placing an intersecting waveguide adjacent to said input waveguide, said intersecting waveguide or said input waveguide having a Bragg grating formed thereon, said input waveguide and said intersecting waveguide separated by a gap distance when in an off state; and
   displacing said Bragg grating sufficiently towards said input waveguide when in an on state such that said Bragg grating can selectively extract a selected one of said plurality of wavelengths.

19. The method of claim 18 wherein said Bragg grating has a periodicity suitable for extracting said one of said plurality of wavelengths into said intersecting waveguide.

20. The method of claim 18 wherein said displacing is performed by an electrically controllable microelectromechanical system (MEMS).

21. The method of claim 18 wherein displacing is performed by an electrostatic moving means for moving said Bragg grating for activating said Bragg grating.

22. A wavelength converter comprising:
   a broadband light source producing light having a plurality of wavelengths;
   a semiconductor optical amplifier that receives said light having a plurality of wavelengths, said semiconductor optical amplifier amplifying said light under the control of a control signal related to a first optical signal at a first wavelength and producing an amplified optical signal; and
   a demultiplexer that receives the output of said semiconductor optical amplifier and extracts from said amplified optical signal at least one of said plurality of wavelengths as an output optical signal at a second wavelength, said demultiplexer comprising:
   (a) an input waveguide for carrying the output of said semiconductor optical amplifier;
   (b) a plurality of intersecting waveguides intersecting with said input waveguide to form a plurality of intersections; and
   (c) a plurality of switches disposed on said plurality of intersections for selectively switching one of said plurality of wavelengths into an associated intersecting waveguide and for selectively transmitting the remaining ones of said plurality of wavelengths.

23. The wavelength converter of claim 22 further including a multiplexer for routing said output optical signal into an output waveguide.

24. The wavelength converter of claim 22 wherein said switches comprise Bragg gratings that have a periodicity suitable for switching said one of said plurality of wavelengths from said input waveguide into an associated one of said intersecting waveguides.

25. The wavelength converter of claim 22 wherein said switches can be engaged to said input waveguide and an associated one of said intersecting waveguides.

* * * * *

UNITED STATES PATENT AND TRADEMARK OFFICE
CERTIFICATE OF CORRECTION

PATENT NO. : 6,608,715 B2
DATED : August 19, 2003
INVENTOR(S) : Jianjun Zhang et al.

It is certified that error appears in the above-identified patent and that said Letters Patent is hereby corrected as shown below:

<u>Column 6,</u>
Line 24, delete dash after "no";

<u>Column 9,</u>
Line 18, comma after "amplifier" should be semicolon;
Line 42, "amplifyng" should be -- amplifying --;

<u>Column 10,</u>
Line 64, add -- or disengaged -- between "engaged" and "to";

Signed and Sealed this

Sixth Day of January, 2004

JAMES E. ROGAN
*Director of the United States Patent and Trademark Office*